United States Patent [19]
Kelly et al.

[11] Patent Number: 5,342,286
[45] Date of Patent: Aug. 30, 1994

[54] WATERPROOF COVERING

[75] Inventors: Joseph L. Kelly, Weems, Va.; Robert S. Jenkins, Boston, Mass.

[73] Assignee: Kellcover, Inc., Charlestown, Mass.

[21] Appl. No.: 171,121

[22] Filed: Jun. 1, 1992

[51] Int. Cl.$^5$ ............................................. A61F 13/00
[52] U.S. Cl. ............................................. 602/3; 602/62
[58] Field of Search ................... 602/3, 63, 62, 60, 61; 383/210, 211, 71, 62, 77, 74; 128/DIG. 15

[56] References Cited

U.S. PATENT DOCUMENTS

| | | |
|---|---|---|
| 1,619,887 | 3/1927 | Sapp . |
| 2,849,171 | 8/1958 | O'Brien, Jr. . |
| 3,186,626 | 11/1963 | Shvetz . |
| 4,036,220 | 6/1977 | Bellasalma .................. 128/DIG. 15 |
| 4,215,687 | 8/1980 | Shaw ............................ 128/DIG. 15 |
| 4,523,586 | 6/1985 | Couri ...................................... 602/3 |
| 4,639,945 | 2/1987 | Betz . |
| 4,727,864 | 3/1988 | Wiesenthal et al. . |
| 4,911,151 | 3/1990 | Rankin .................................. 602/3 |
| 4,966,135 | 10/1990 | Renfrew ............................... 602/3 |
| 5,046,621 | 9/1991 | Bell ..................................... 383/211 |
| 5,186,988 | 2/1993 | Dixon .................................. 383/71 |

Primary Examiner—Robert A. Hafer
Assistant Examiner—David J. Kenealy
Attorney, Agent, or Firm—Lowe, Price, LeBlanc & Becker

[57] ABSTRACT

A water impervious covering for extremities is described. The covering is intended to protect a bandage or cast portion of the extremity during bathing or the like. The covering is a sack-like member having an upper lip extending above the opening in the covering. The lip has a laterally extending perforation parallel to the opening extending approximately four-fifths of the width thereof. An adhesive strip extends the entire width of the lip from one side to the other. The adhesive strip is covered with a protective removable sheet. In use, the perforation is torn to separate the lip into a tie member and a securing member. The adhesive protective sheet is then removed and the extremity inserted into the sack-like covering. The securing portion then is adhered to the surface of the extremity and the opening gathered around the extremity so that the tie member may be used to encircle the gathering and thereby secure the covering to the extremity.

8 Claims, 2 Drawing Sheets

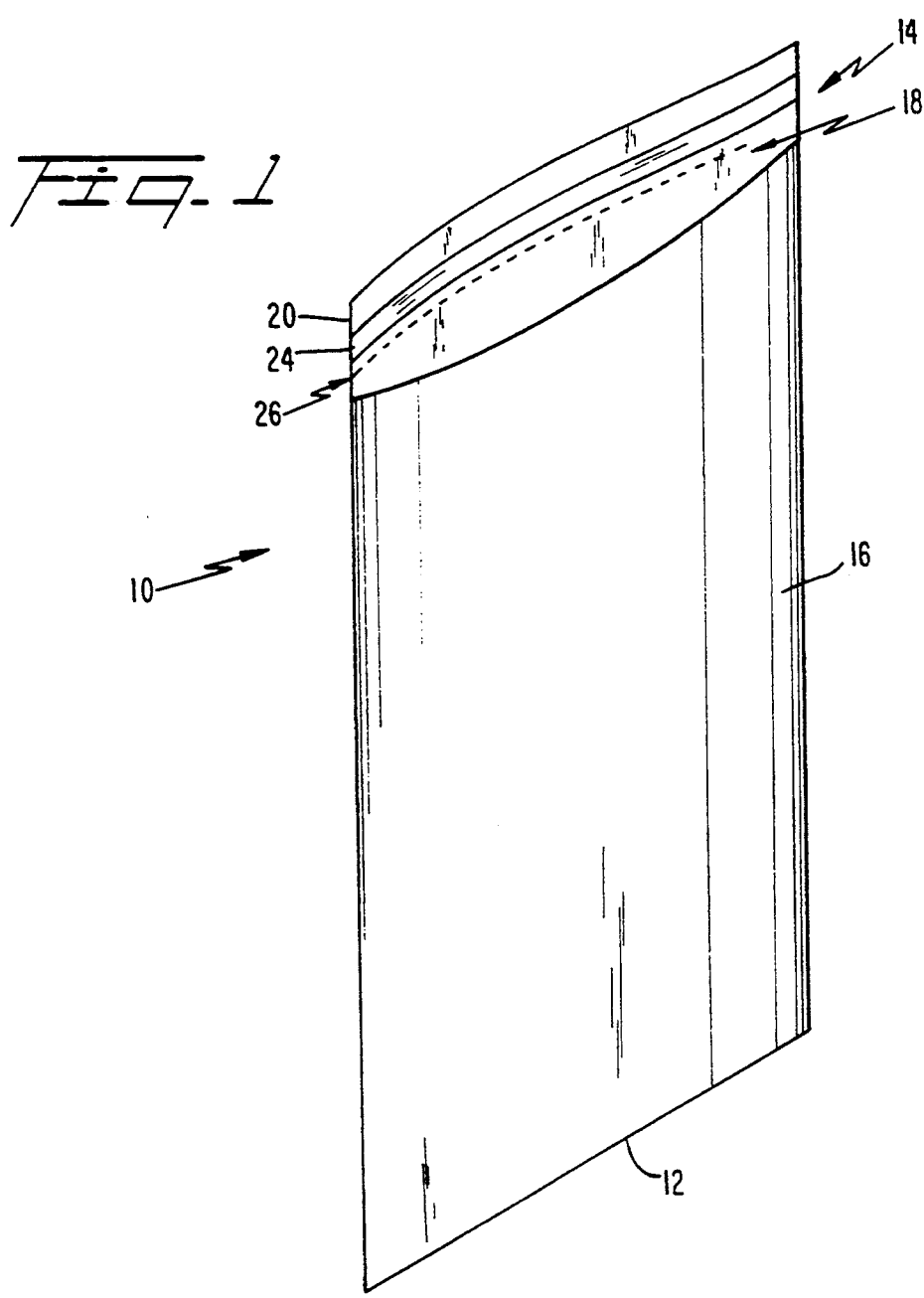
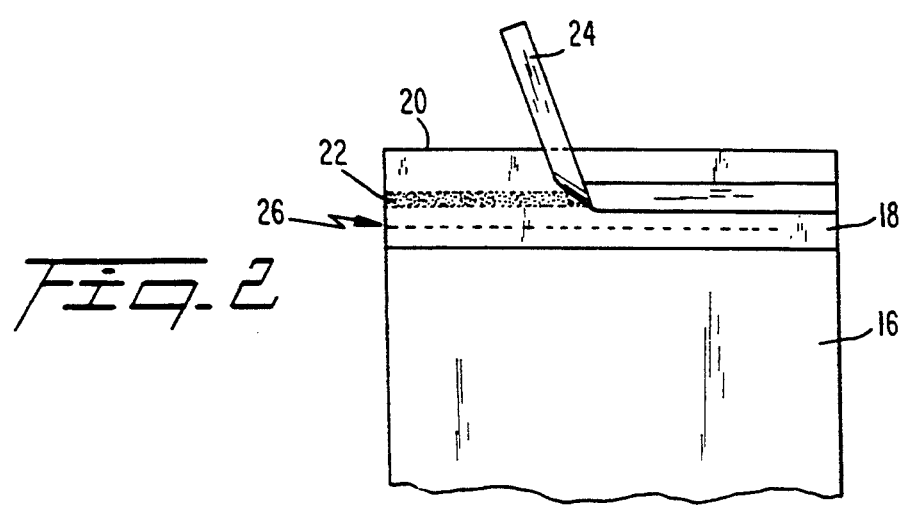

WATERPROOF COVERING

FIELD OF THE INVENTION

This invention relates to a waterproof covering for bandages or casts applied to extremities and, in particular, to a disposable sack-like member for enclosing the extremity including the bandage or cast and having a tie for securing the device against penetration by water when the wearer is bathing, showering or the like.

BACKGROUND OF THE INVENTION

As is well known, a cast or bandage on an extremity for a lengthy period of time can be a source of great discomfort. Due to the necessity of keeping the cast or bandage dry, bathing, showering, or the like can be difficult. Furthermore, if a water impervious covering is used, it must be highly efficient because if water penetrates, for example, around the opening of a cast, patient discomfort will result in the form of itching, infection, or the like.

It is known to provide a sack-like member constructed of plastic sheeting material such as polyethylene for use in covering such extremity bandages. Such a device is shown in U.S. Pat. No. 4,727,864 wherein a sack-like member is intended to receive the extremity and a tie member is attached at one end thereof to the upper portion. The exposed portion of the tie member, as well as a spot on the sack edge, are coated with an adhesive. It is intended, then, that the tie member encircle the extremity so that the adhesive will seal the interface between the covering opening and the patient's skin against the penetration of water. This device is relatively expensive to manufacture in that a separate tie member must be welded at one end thereof to the opening of the container, and the adhesive applied both within the opening of the container at a spot, and along the length of the exposed portion of the tie.

It is also well known to provide tie members with food storage or garbage sacks which are of plastic material. For example, in U.S. Pa. No. 2,849,171, a tie member separate from the sack is provided on the upper portion thereof extending from side to side and the tie member is welded at each end to the sack. A loop, then, is formed by folding the tie member in the center which is used to tie the sack shut after it has been filled. Clearly, this would not be universally adaptable to covering extremities in that the loop would have to be very long and two hands would be required to tie the loop. If the extremity is a leg, then one could, presumably, tie the device. However, if the extremity injured is an arm, it would not be possible to tie such a device with one hand. Similarly, U.S. Pat. No. 3,186,626 describes integral tie members which are torn from the opening at either side thereof of a food storage sack. The tie men%bets, then, are tied in a standard knot to close the sack opening. This also would require two hands and, therefore, it would not be universally applicable to injured persons without regard to whether the injury is located on the arm or leg.

SUMMARY OF THE INVENTION

It has been discovered, however, that an effective and efficient covering member can be provided which can be easily secured with one hand. The covering of this invention is a plastic sack-like member having a front and a back either secured at the edges thereof, or formed from tubular material, and having a closed end and an open end. The open end of the cover of this invention includes an extended lip along one side thereof which lip has a laterally extending strip of adhesive covered with a protective covering. The lip further is perforated along a substantial length thereof so that when the perforation is ripped, a tie member will be formed which is integral with the covering and when the protective covering is removed from the adhesive, the tie member, and the integral portion of the sacking extending therefrom along the lip will have an exposed adhesive coating.

The method of using the device of this invention, then, includes extending the extremity into the sack-like portion whereby the adhesive on the tie will hold the sack-like member of this invention by adhering it to the extremity it is wrapped around. The remaining portion of the opening may then be gathered around the extremity, and the tie member looped therearound to adhesively seal the opening of the sack against the patient's skin.

Accordingly, it is an object of this invention to provide a disposable water impervious covering material for extremities which can be universally applicable to both arms and legs in that a single tie member is provided which is integral to the sack and which is coated with adhesive so that it may be used to close the sack opening around the extremity and to be secured with a single hand.

It is yet another object of this invention to provide a method for maintaining a bandage or cast on an extremity in a dry condition while showering or bathing which includes the steps of providing a water impervious bag having an integral, single tie member formed on the open end, which comprises a perforation along the length of the lip which has the adhesive strip adhered thereto. The method includes partially separating the integral strip or tie from the bag, inserting the extremity into the bag, removing the protective backing from the adhesive strip, securing the unperforated portion to the extremity and winding the tie around the extremity to secure the opening of the bag thereto against the admittance of water.

BRIEF DESCRIPTION OF THE DRAWING

These and other objects will become readily apparent with reference to the drawings and following description wherein:

FIG. 1 is a perspective view of the covering of this invention.

FIG. 2 is a fragmentary front view showing the adhesive strip and tie member at the open end of the covering of FIG. 1.

DESCRIPTION OF THE INVENTION

Figure 3:
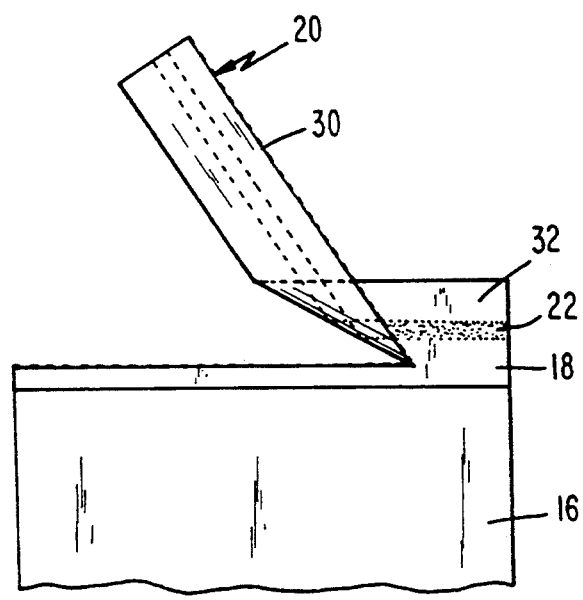
FIG. 3 is a view similar to FIG. 2 showing the integral tie member separated from the covering.

With attention to the drawings, the covering member of this invention 10 is preferably constructed of plastic sheeting material and configured as a sack having a closed bottom 12 and open top 14, a front panel 16 and a back panel 18. Back panel 18 defines an upstanding lip 20 intended to extend a substantial length beyond the opening 14 of the sack member 10.

The lip 20 integral with the back panel 18 mounts a longitudinally extending adhesive strip 22 extending the entire width thereof and spaced above the opening 18. The adhesive strip 22 is normally covered with a protective, separable covering strip 24 to preserve the tackiness of the adhesive strip 22. As is well known to those skilled in the art, protective strip 24 may be a coated paper, or the like, and is intended to be readily separable from the underlying adhesive strip 22 by hand.

The lip 20, integral with the back 18, also has a perforation 26 which extends from one side substantially across the lateral extent of the lip 20, preferably about four-fifths thereof, as shown in FIGS. 2 and 3. The lip 20 forms a tie member when the perforation is used to separate that portion thereof from the back panel 18 as by tearing by hand. See FIG. 3. When the perforation is torn, as shown in FIG. 3, a tie member 30 is formed and an integral securing portion 32 also formed from lip 20, as will be subsequently explained. The tie member 30 has the adhesive strip 22 extending the length thereof, and the integral securing portion 32 also has the adhesive strip 22 extending therealong.

In order to utilize the device of this invention, the covering 10 is used to cover that portion of the extremity which is bandaged or has a cast thereon. In order to do so, the hand or foot is inserted through the opening 14 into the sack member 10. The perforation 26 is then torn forming the integral tie member 30 and the adhesive strip covering 24 is removed, exposing the tacky adhesive strip 22 therealong.

Figure 4:
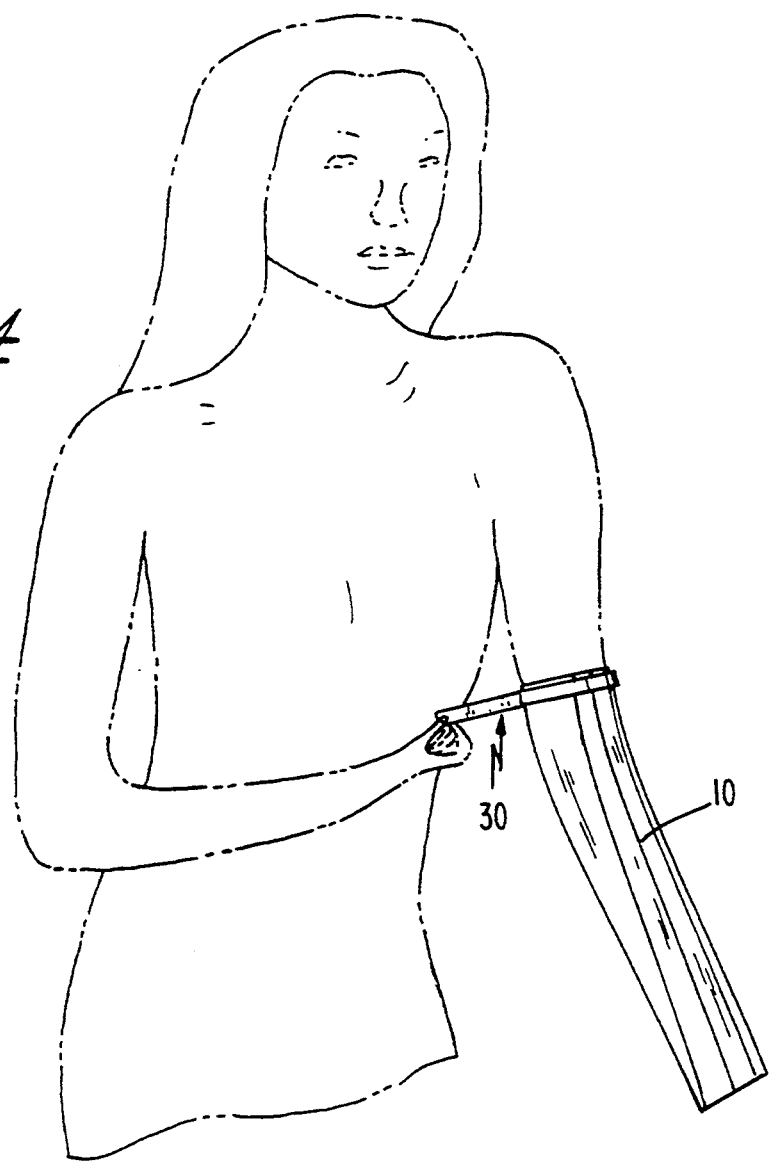
FIG. 4 is a representation of the covering member mounted on an arm with the tie member positioned to secure the covering of this invention to the arm.

The adhesive on securing segment 32 is then used to secure the sack member 10 to an adjacent portion of the extremity. With reference to FIG. 4, the securing portion 32 would be hidden behind the arm but affixed to the arm. The tie member 32 is then used to gather the opening 14 around the extremity and secure the same by passing the tie member 30 around the extremity and the covering member opening 14. In this way, the tie member 30 can be used to draw the periphery of the opening into gathers around the extremity and then pass therearound so that the adhesive member firmly secures the opening 18 around the extremity against water or the like.

When the device is removed, it is merely necessary to separate the adhesive on the securing portion 32 from the skin surface of the extremity and loosen the tie member 30 so that the entire covering 10 can be removed.

As will be apparent to those skilled in the art, whether the extremity to be covered is an arm or a leg, the device of this invention can be secured with one hand. In order to do so, it is necessary that the securing portion 32 and its adhesive strip secure the covering 10 against the skin so that as the periphery of opening 18 is gathered, the covering will not slip downwardly or laterally. The adhesive on the tie member 30, then, merely secures the gathers of the periphery of opening 18 to the extremity itself as it is tightened by pulling against the previously secured portion 32.

It is intended that the device of this invention be constructed of light-weight plastic material which is water impervious. The adhesive strip is also intended to be formed of an adhesive compatible with human skin and the dimensions of the device of this invention may be changed, depending upon whether it is intended to cover an entire extremity, an arm or a leg, or merely a hand or a foot. The covering 10 may be formed of tubular material and welded to form the closed bottom 12 or it may be formed of sheeting material folded to form one longitudinal edge and welded to form the closed bottom and opposite longitudinal edge. The construction of the device will be obvious to those skilled in the art. While it is preferred to construct the device of this invention of polyethylene sheeting material, the invention is not intended to be limited to the particular materials of construction or the process used for forming the sack-like covering member 10. The perforation 26 which separates the lip 20 from the back 18 to form the tie member 30 and the securing portion 32 preferably extends about four-fifths of the width of the covering 10, and this invention is not intended to be limited to a particular length of the perforation 26.

The invention may be embodied in other specified forms without departing from the spirit or essential characteristics thereto. The present embodiments are therefore to be considered in all respects as illustrative and not restrictive, the scope of the invention being indicated by the appended claims rather than by the foregoing description, and all changes which may come within the meaning and range of equivalency of the claims are therefore intended to be embrace therein.

We claim:

1. A waterproof covering for an extremity comprising:

a sack-like member of water impervious material having a front panel and a back panel, said front and back panel interconnected to form a closed bottom, an open top and opposing edges, said front and back panels being upstanding to define said open top for receiving said extremity; said back panel including a lip as an integral part thereof, said lip extending upwardly from and beyond the open top such that free opposing ends of said lip are aligned with respective said opposing edges of said sack-like member so that said lip is between said opposing edges; an adhesive strip extending laterally across the length of said lip; removable means covering said strip for protecting said adhesive; and a perforation line formed in said lip and having a length less than the length of said lip to form an integral tie member having a free end as one of said free opposing ends of said lip and a securing tie member segment integral with said tie member and said back panel, said adhesive strip extending the length of said tie member and securing segment.

2. The covering of claim 1 wherein said adhesive strip extends laterally across said lip parallel to the open top of said sack member.

3. The covering of claim 2 wherein said lip has an upper edge extending the length thereof parallel to the open top of said sack-like member and said adhesive strip is disposed between the open top and upper edge.

4. The covering of claim 1 wherein said perforation line is disposed between said adhesive strip and the open top of said sack-like member.

5. The covering of claim 1 wherein said tie member is about four times longer than said securing segment.

6. The covering of claim 5 wherein said perforation extends about four-fifths of the length of said lip.

7. Method for protecting extremities having bandages or casts thereon from moisture comprising the steps of:

providing a sack-like member of water impervious material having a front panel and a back panel interconnected to form an open top, a closed bottom and opposing upstanding edge, a lip as an integral part of said back panel, said lip extending upwardly from and beyond the open top and between said interconnecting upstanding edges such that opposing free ends of said lip are aligned with respective said opposing upstanding edges, an adhesive strip extending laterally along the length of said lip, a protective means removably covering said adhesive strip and a perforation line formed in said lip and having a length less than the length of said lip to form an integral tie member having a free end as one of said opposing free ends and a securing tie member segment integral with said back panel and said tie member;

extending the extremity into the member through the open top; removing the protective means to expose the adhesive strip and securing the segment portion of said lip to the extremity therewith;

separating the tie member portion from the back panel;

gathering the open top about the extremity; wrapping the tie member therearound; and securing the same with the adhesive strip thereon.

8. The method of claim 7 wherein the perforated line extends about four-fifths the length of said lip.

* * * * *

UNITED STATES PATENT AND TRADEMARK OFFICE
CERTIFICATE OF CORRECTION

PATENT NO. : 5,342,286
DATED : August 30, 1994
INVENTOR(S) : Joseph L. KELLY

It is certified that error appears in the above-indentified patent and that said Letters Patent is hereby corrected as shown below:

On the title page of the patent delete "[21] Appln. No.: 171,121" and insert the correct Application Serial No. as follows:
--- [21] Appln. No.: 891,121 ---.

Signed and Sealed this

Twenty-seventh Day of December, 1994

Attest:

BRUCE LEHMAN

Attesting Officer     Commissioner of Patents and Trademarks